(12) United States Patent
Alon et al.

(10) Patent No.: US 9,220,688 B2
(45) Date of Patent: Dec. 29, 2015

(54) DEVICE AND METHOD FOR REDUCING CALORIE INTAKE

(75) Inventors: Amir Alon, Hod Hasharon (IL); Itzhak Katz, Petach Tikva (IL); Benjamine Alspector, Mevaseret (IL); Abraham J. Domb, Efrat (IL)

(73) Assignee: SLENDINE SA, Mezzovico-Vira (CH)

( * ) Notice: Subject to any disclaimer, the term of this patent is extended or adjusted under 35 U.S.C. 154(b) by 0 days.

(21) Appl. No.: 12/757,843

(22) Filed: Apr. 9, 2010

(65) Prior Publication Data

US 2010/0215733 A1  Aug. 26, 2010

Related U.S. Application Data

(63) Continuation of application No. 11/581,175, filed on Oct. 16, 2006, now abandoned, which is a continuation of application No. PCT/IL2005/000154, filed on Feb. 8, 2005.

(60) Provisional application No. 60/542,843, filed on Feb. 10, 2004.

(51) Int. Cl.
  *A61K 9/48* (2006.01)

(52) U.S. Cl.
  CPC .................................... *A61K 9/4808* (2013.01)

(58) Field of Classification Search
  CPC ...................................................... A61K 9/4808
  See application file for complete search history.

(56) References Cited

U.S. PATENT DOCUMENTS

| | | | | |
|---|---|---|---|---|
| 3,485,235 | A | * | 12/1969 | Ronald .......................... 600/582 |
| 3,797,492 | A | | 3/1974 | Place |
| 3,844,285 | A | | 10/1974 | Laby |
| 4,207,890 | A | | 6/1980 | Mamajek et al. |
| 4,268,497 | A | | 5/1981 | Griffin et al. |
| 4,308,250 | A | | 12/1981 | Griffin et al. |
| 4,416,267 | A | | 11/1983 | Garren et al. |
| 4,432,968 | A | | 2/1984 | Page et al. |
| 4,434,153 | A | | 2/1984 | Urquhart et al. |
| 4,592,339 | A | | 6/1986 | Kuzmak et al. |
| 4,763,653 | A | | 8/1988 | Rockey |
| 4,767,627 | A | | 8/1988 | Caldwell et al. |
| 4,812,315 | A | | 3/1989 | Tarabishi |
| 5,306,300 | A | | 4/1994 | Berry |
| 5,326,564 | A | * | 7/1994 | LaRosa et al. ................ 424/401 |
| 5,345,949 | A | | 9/1994 | Shlain |
| 5,971,942 | A | * | 10/1999 | Gu et al. ....................... 600/582 |
| 6,120,803 | A | | 9/2000 | Wong et al. |
| 6,488,962 | B1 | | 12/2002 | Berner et al. |
| 6,543,456 | B1 | | 4/2003 | Freeman |
| 6,558,400 | B2 | | 5/2003 | Deem et al. |
| 6,627,206 | B2 | | 9/2003 | Lloyd |
| 6,635,281 | B2 | | 10/2003 | Wong et al. |
| 6,677,318 | B1 | | 1/2004 | Beisel |
| 6,685,962 | B2 | | 2/2004 | Friedman et al. |
| 6,776,999 | B1 | | 8/2004 | Krumme |
| 6,981,980 | B2 | | 1/2006 | Sampson et al. |
| 7,449,001 | B2 | * | 11/2008 | Stoltz ............................ 600/582 |
| 7,611,480 | B2 | | 11/2009 | Levy |
| 8,722,066 | B2 | | 5/2014 | Costa |
| 2003/0072804 | A1 | | 4/2003 | Hird et al. |
| 2007/0202152 | A1 | | 8/2007 | Drouillard et al. |
| 2007/0207186 | A1 | | 9/2007 | Scanlon et al. |
| 2007/0293426 | A1 | | 12/2007 | Demuth |
| 2008/0089933 | A1 | | 4/2008 | Alon et al. |
| 2008/0241094 | A1 | * | 10/2008 | Burnett et al. ............. 424/78.01 |
| 2009/0028996 | A1 | | 1/2009 | Yamka et al. |
| 2009/0035367 | A1 | | 2/2009 | Mintchev et al. |
| 2010/0196470 | A1 | | 8/2010 | Alon et al. |
| 2011/0295299 | A1 | | 12/2011 | Braithwaite et al. |
| 2014/0276330 | A1 | | 9/2014 | Costa |
| 2015/0030639 | A1 | | 1/2015 | Costa |

FOREIGN PATENT DOCUMENTS

| | | |
|---|---|---|
| CN | 104640604 | 5/2015 |
| WO | WO 02/102243 | 12/2002 |
| WO | WO 2005/074378 | 8/2005 |
| WO | WO 2010/063466 | 6/2010 |
| WO | WO 2010/110882 | 9/2010 |

(Continued)

OTHER PUBLICATIONS

Lambert et al "Autonomous telemetric capsule to explore the small bowel," Med. & Biol. Eng. & Compt., 1991, 29, 191-196.*

(Continued)

*Primary Examiner* — Suzanne Ziska

(74) *Attorney, Agent, or Firm* — Lewis Roca Rothgerber LLP

(57) ABSTRACT

Devices and methods for substantially reducing the caloric efficiency of the digestive tract by capturing food being digested in the stomach 10 and/or anywhere else in the gastrointestinal (GI) tract, absorbing or encapsulating the captured food into multiple capturing members and moving such multiple capturing members containing the ingestible encapsulated food down the GI tract, practically out of reach of the GI absorption organs, thus excluding the entrapped ingredients from being involved in the digestion and\or absorption process. The device is designed for oral delivery. The system can be comprised of liquid, food bars or a capsule system. The capsule system is comprised of an external capsule that dissolves in accordance with a temporal or ph dependent preset, which allows the food intake to be at least partially fluidic. The capsule system is further comprised of a mechanism designed to capture and isolate a portion of the food being digested.

16 Claims, 9 Drawing Sheets

(56) References Cited

FOREIGN PATENT DOCUMENTS

| WO | WO 2011/038949 | 4/2011 |
|---|---|---|
| WO | WO 2013/148359 | 10/2013 |

OTHER PUBLICATIONS

PCT Patent Application No. PCT/IL2005/000154 filed Feb. 8, 2005 in the name of Katz, International Search Report and Written Opinion mailed Aug. 30, 2009.
U.S. Appl. No. 12/757,841, filed Apr. 9, 2010 in the name of Alon et al., non-final Office Action mailed May 26, 2010.
PCT Patent Application No. PCT/US2010/000872 filed Mar. 23, 2010 in the name of Costa, International Search Report and Written Opinion mailed May 17, 2010.
U.S. Appl. No. 11/581,175, filed Oct. 16, 2006 in the name of Alon et al., non-final Office Action mailed Jun. 22, 2010.
U.S. Appl. No. 11/581,175, filed Oct. 16, 2006 in the name of Alon et al., final Office Action mailed Dec. 7, 2010.
U.S. Appl. No. 12/757,841, filed Apr. 9, 2010 in the name of Alon et al., final Office Action mailed Dec. 8, 2010.
Bhattarai et al., "Chitosan-based hydrogels for controlled, localized drug delivery", Advanced Drug Delivery Reviews 62 (2010) pp. 83-99.
Lee et al., "Review: Biomedical applications of callagen", International Journal of Pharmaceutics 221 (2001) pp. 1-22.
MedlinePLus, "Nitrofurantoin", Feb. 22, 2010, pp. 1-3, <http://www.nlm.nih.gov/medlineplus/druginfo/meds/a682291.html>.
PCT Application No. PCT/US2013/032513 International Search Report and Written Opinion dated Jun. 17, 2013.
U.S. Appl. No. 13/431,076 Final Office Action mailed Oct. 10, 2013.
U.S. Appl. No. 13/431,076 Office Action mailed Mar. 12, 2013.
U.S. Appl. No. 14/272,342 Office Action mailed Jan. 15, 2015.
U.S. Appl. No. 14/272,342 Final Office Action mailed Aug. 12, 2015.
U.S. Appl. No. 13/841,138 Office Action mailed Sep. 11, 2015.

* cited by examiner

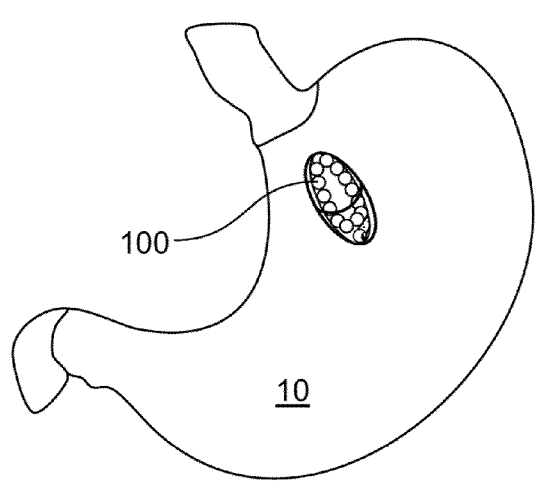
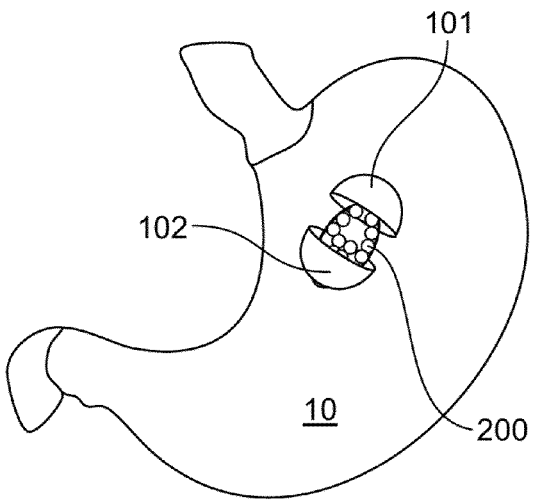
*Fig. 4a*   *Fig. 4b*
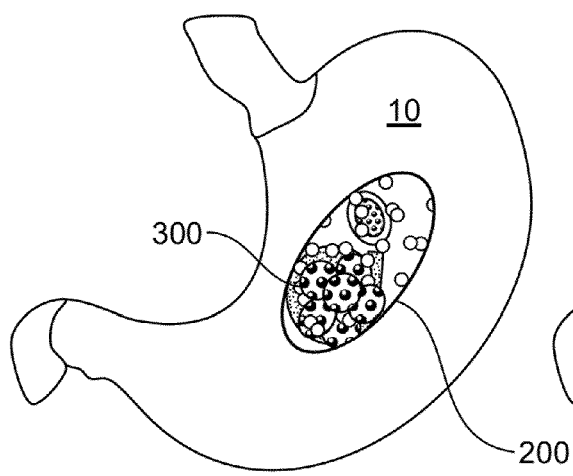
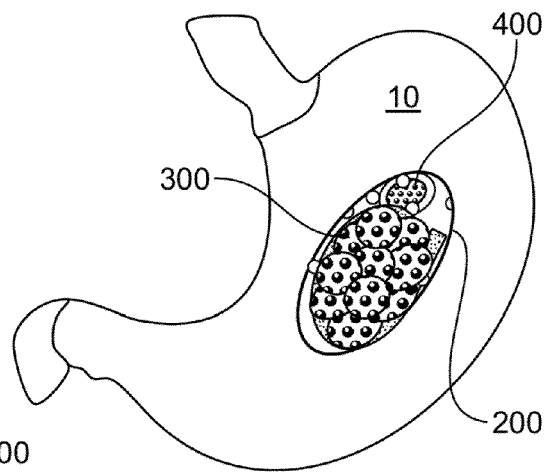
*Fig. 4c*   *Fig. 4d*

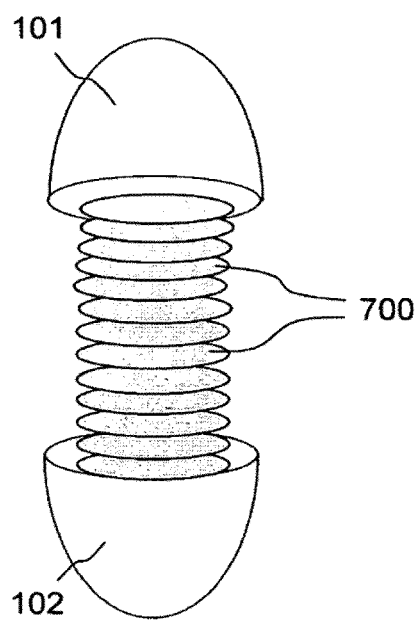
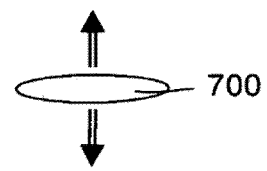
Fig. 8b
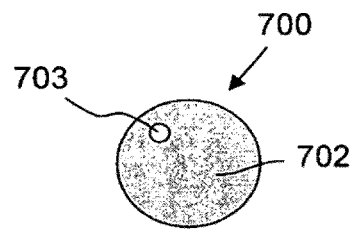
Fig. 8c
Fig. 8a

DEVICE AND METHOD FOR REDUCING CALORIE INTAKE

CROSS-REFERENCE TO RELATED APPLICATIONS

This present application is a continuation of U.S. patent application Ser. No. 11/581,175, which claims the benefit of PCT application no. PCT/IL05/00154 filed on Feb. 8, 2005, which claims the benefit of U.S. provisional application No. 60/542,843 filed on Feb. 10, 2004 all of which are incorporated herein by reference in their entireties.

FIELD OF THE INVENTION

The present invention relates in general to a device and method for substantially reducing the caloric efficiency of the digestive tract by capturing food being digested in the stomach and/or anywhere else in the GI tract, into entrapping members; moving the entrapping member containing said food down the GI tract, thus excluding at least part of the food intake from being absorbed in the small intestine and further down the GI tract.

BACKGROUND OF THE INVENTION

Obesity is a chronic disease due to excess fat storage, a genetic predisposition, and strong environmental contributions. This problem is worldwide, and the incidence is increasing daily. There are medical, physical, social, economic, and psychological comorbid conditions associated with obesity. There is no cure for obesity except possibly prevention. Non-surgical treatment has been inadequate in providing sustained weight loss. Currently, surgery offers the only viable treatment option with long-term weight loss and maintenance for the morbidly obese. Surgeries for weight loss are called bariatric surgeries. There is no one operation that is effective for all patients. Gastric bypass operations are the most common operations currently used. Because there are inherent complications from surgeries, bariatric surgeries should be performed in a multidisciplinary setting. The laparoscopic approach is being used by some surgeons in performing the various operations. The success rate—usually defined as >50% excess weight loss that is maintained for at least five years from bariatric surgery—ranges from 40% in the simple to >70% in the complex operations. The weight loss from surgical treatment results in significant improvements and, in some cases, complete resolution of comorbid conditions associated with obesity. Patients undergoing surgery for obesity need lifelong nutritional supplements and medical monitoring.

It is accepted that patients suffering from obesity are at a substantially increased risk of medical ailments and a range of diseases, including: Type II diabetes, heart disease, stroke, high blood pressure, high cholesterol, certain cancers, and other disorders. Furthermore, patients suffering morbid obesity have life expectancy that is significantly reduced, by at least ten to fifteen years.

For patients suffering from extremely severe obesity (morbid obesity), i.e. for patients whose weight exceeds the ideal weight by at least 50 kilograms, for example, it is absolutely essential to operate surgically on such patients in order to avoid not only a series of health problems that stem from such obesity, but also to avoid certain and imminent death of such patients.

It has also been observed that treatment based on a severe diet combined with a series of physical exercises associated with a change in behavior, in particular eating behavior, are relatively ineffective in such cases of morbid obesity, even though such methods of treatment are the most healthy.

Methods that have been used in the prior art to treat obesity include gastric bypasses and small-bowel bypasses such as described in U.S. Pat. No. 6,558,400 and U.S. Pat. No. 6,543,456. The number of these bariatric surgeries has skyrocketed from 40,000 per year back then to 120,000 in 2002. Many complications are associated with these procedures. Many patients have suffered serious side effects and regret having had it.

Other methods aim at reducing the effective volume of the stomach to induce a satiety feeling by the patient and hence reducing the calorie intake per meal.

One such method is the stapling of portions of the stomach has also been used to treat obesity, such as described in U.S. Pat. No. 5,345,949. This includes both vertical and horizontal stapling and other variations trying to reduce the size of the stomach or make a small stoma opening. Many problems have been associated with the use of staples. First, staples are undependable; second, they may cause perforations; and the pouch or stoma opening formed by the staples becomes enlarged over time making the procedure useless.

Another method that has been developed is the placement of an inflatable bag or balloon into the stomach causing the recipient to feel "full". Such a procedure has been described in the patent to Garren et al U.S. Pat. No. 4,416,267. The balloon is inflated to approximately 80% of the stomach volume and remains in the stomach for a period of about three months or more. This procedure, although simple, has resulted in intestinal blockage, gastric ulcers, and even in one instance, death and fails to address the problems of potentially deleterious contact with the gastric mucosa which can result from leaving an inflated bag in the stomach for an extended period of time. Moreover, it also failed to produce significant weight loss for long periods of time.

Yet another method employs the placement of a band around a portion of the stomach thereby compressing the stomach and creating a stoma opening that is less than the normal interior diameter of the stomach for restricting food intake into the lower digestive portion of the stomach. Kuzmak et al in U.S. patent have described such a band. U.S. Pat. No. 4,592,339. It comprises a substantially non-extensible belt-like strap, which constrictively encircles the outside of the stomach thereby preventing the stoma opening from expanding. Kuzmak et al also describe bands, which include a balloon-like section that is expandable and deflatable through a remote injection site. The balloon-like expandable section is used to adjust the size of the stoma opening both intra-operatively and post-operatively.

Complications have been observed with both inflatable and non-inflatable gastric bands. In particular, obstruction of the stoma from edema and migration of the band has been observed. Such edema-caused obstruction of the stoma may be due to excessive vomiting. In these cases, the stoma must be enlarged either by deflating the expandable portion of a band or by removing the band altogether.

Yet another method is to impose satiety. U.S. Pat. No. 6,677,318, describing a swellable sponge-like structure. These structures are swallowed by the patient being collapsed inside a capsule. The capsule dissolves in the stomach and the polymer structure with super absorbing characteristics; absorb the gastric juices, which cause the structure to swell considerably. This patent aims to reduce food intake by causing the recipient to feel "full", yet the absorbed content of the sponge is finally digested.

Lipase inhibition as a mean for reducing lipid intake is well known in the art, the major draw back is the oily stool as a side effect. To overcome this side effect, polymers capable of absorbing lipids where introduce, as in U.S. Pat. No. 4,432, 968, but as the absorption is reversible and shifted backwards as a result of bile salt emulsifier, the overall entrapment was quite poor.

In order to overcome the a forth mentioned drawbacks, the present invention relates on a lipid absorption polymer having an prolonged equilibrium period in the range of 4-8 hours so as to keep the absorption step active during the relevant period in the digestion tract.

It is then the object of this invention to overcome these and other deficiencies described above.

SUMMARY OF THE INVENTION

The invention seeks to provide a successful and non-invasive alternative to existing approaches for controlling obesity.

The invention objective is to substantially reduce the caloric efficiency of the digestive tract by capturing food being digested in the stomach and/or anywhere else in the GI tract into entrapping members; moving the entrapping member containing the entrapped food ingredients down the gastrointestinal tract, thus excluding at least part of the entrapped food from being absorbed in the small intestine.

Another objective of this invention is to introduce a lipid absorption polymer having an prolonged equilibrium period in the range of 4-8 hours so as to keep the absorption step active during the relevant period in the digestion tract.

Another objective of this invention is to interfere with the micelles formation and capture the free lipids contained within.

Another objective of this invention is to provide a delivery system of the material via means of compressing the material so that it takes less space in the intake, and when the capsule, for example, opens up or dissolves, the individual particles of the material expand to accommodate the captured liquids.

In one embodiment, the device is comprised of a capsule system for oral delivery. The capsule system is comprised of an external capsule made of gelatin—as an example that dissolves in accordance with a temporal preset, which allows the food intake to be at least partially fluidic. The capsule system is further comprised of an internal permeable bag having a structure such as meshed, woven or fibers, made of disintegrable material such as gelatin for example, which bag contain expandable, super absorbent beads, which dry beads are larger than the pores of the bag, which bag is inflatable. When the bag comes in contact with the fluidic content of the stomach, fluids penetrate into the bag. The fluids are absorbed by the expandable, hydrogel beads enclosed. These beads expand partially or until they reach the absorption capacity limit. Optionally, the internal bag further contains a coating capsule, which dissolves at this time and coats the expandable beads, to seals and protects them from disintegration or prevent leakage of entrapped liquid, throughout their journey out of the GI tract.

For the sake of clarity, a capsule is a sealed container and a hag is a permeable containers.

In other embodiments, the external capsule contains folded mechanical structures, which open up to captures some of the stomach content and protects them from disintegration throughout their journey through and out of the GI tract.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings, which are given by way of illustration only and thus not limitative of the present invention.

FIG. 2c is a view of an expandable bead.

FIG. 2d is a view of a coating capsule.

FIG. 4a illustrates of the capsule system entering the stomach at t1.

FIG. 4b illustrates the external capsule dissolving at t2.

FIG. 4c illustrates the expandable beads expanding as they absorb stomach fluids.

FIG. 4d illustrates the expandable beads reaching the size limits of the internal bag at t4.

FIGS. 8a-c illustrates yet another embodiment of the invention.

DETAILED DESCRIPTION OF PREFERRED EMBODIMENTS

Figure 1:
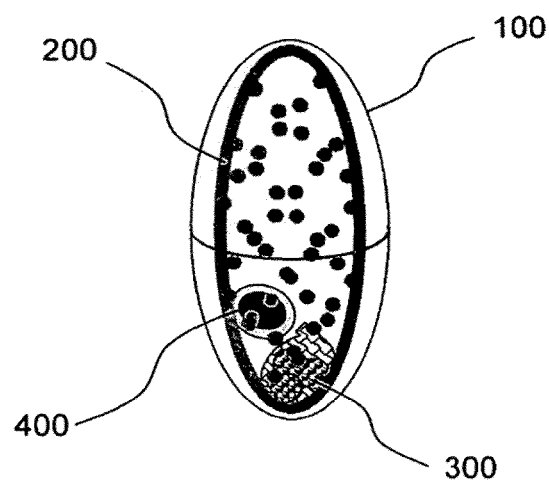
FIG. 1 is a view of the assembled device.

Before explaining embodiments of the invention in detail, it is to be understood that the invention is not limited in its application to the details of construction and the arrangement of the components set forth in the following description or illustrated in the drawings.

Unless otherwise defined, all technical and scientific terms used herein have the same meaning as commonly understood by one of ordinary skill in the art to which this invention belongs. The materials, methods, and examples provided herein are illustrative only and not intended to be limiting.

Figure 3:
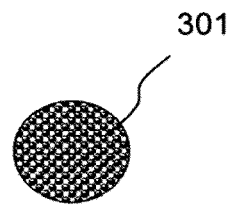
FIG. 3 illustrates a basic embodiment of this invention depicting an outer capsule containing super absorbent expandable beads.
Figure 3:
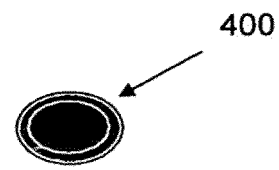
Figure 3:
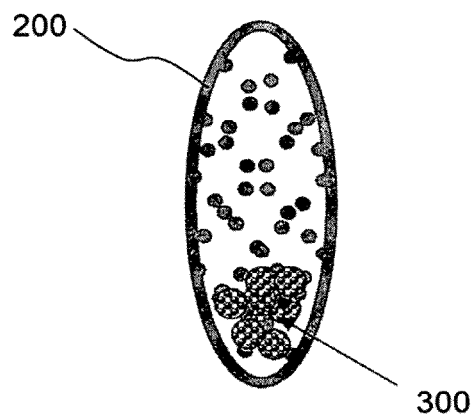

In accordance with one basic embodiment of the present invention, illustrated in FIG. 3, the device is in a form of a pill comprises an outer capsule 200 made of Gelatin for example, which capsule 200 is at least partly filled with cross-linked polymer beads, such as Hydrogels, supper absorbent polymers, cross-linked polymers, known in the art, which beads having a diameter in the range of microns to few mm and are made of non toxic and non digestible polymer and are capable of absorbing fluids at a ratio of at least 5:1 (W/W), (liquid\bead) by diffusion, osmotic force, ionic interaction, and\or capillary force, and\or magnetic force, or other physic-chemical mechanism, such as polyacryl amid derivatives, which absorbing beads may also act as ion exchanger, exclusion gel such as a cross-linked polydextran (or possibly Cellulose Ethers like material), which beads optionally may also contain functional groups that improves permeability when the ambient is acidic (low pH—at the stomach), yet the permeability is reduced when the ambient pH is neutral or basic (small intestine).

In practice, the pill is ingested, and the capsule 100 dissolves at a temporal preset, beads 300 which are now in contact with the content of the food being digested, absorbs caloric enriched liquid and swells. Next the beads along with content of the stomach 10 are moved into the small intestine, where the entrapped content of the beads are practically not involved in the digestion and absorbing steps in the intestine. It is plausible to design the beads such that they will continue to absorb digested food in the small intestine and further down the GI tract.

In another embodiment, similar to the first embodiment, the beads are pre coated or pre absorbed by a composition capable of forming at least a partial nutrient barrier on small intestine. The composition helps further to reduce the absorption of food in case of leaking from the bead.

FIG. 1 is a view of the assembled capsule system. It comprises an external capsule 100 which can be made of a biocompatible material such as gelatin, an internal bag 200 which can be made from gelatin with a net like structure, absorbing beads 300 which can be made from Hydrogels and coating capsule(s) 400.

Figures 2A, 2B:
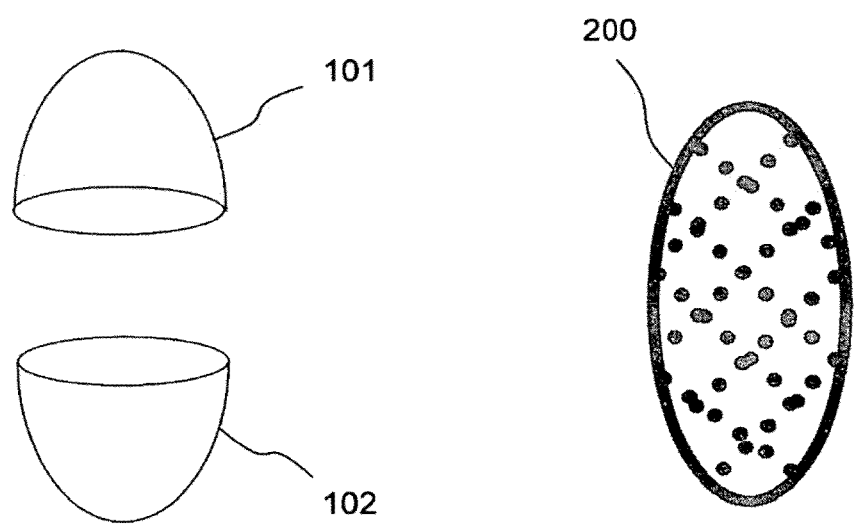
FIG. 2a is a view of the external capsule.
FIG. 2b is a view of the internal bag.
Figure 5:
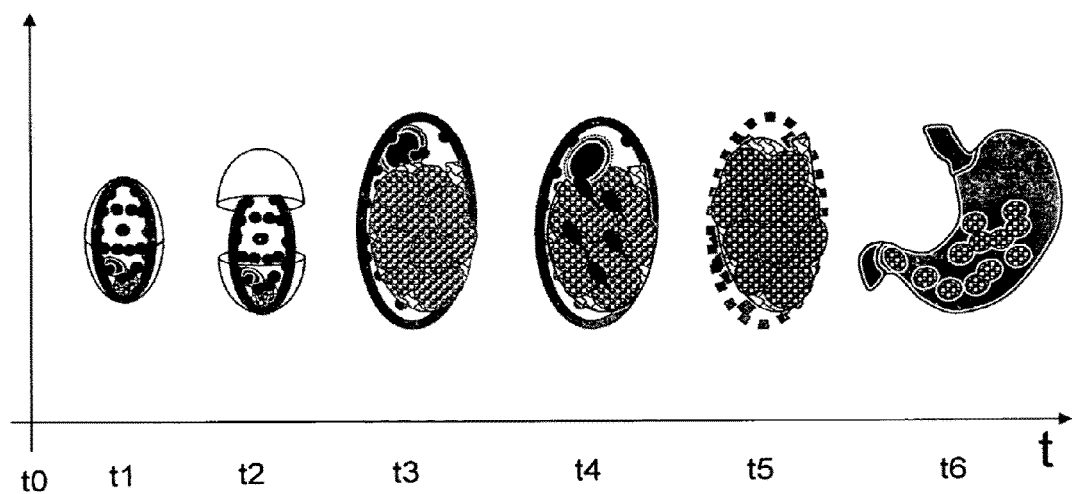
FIG. 5 is a temporal illustration of a full cycle of the process.
Figure 6A:
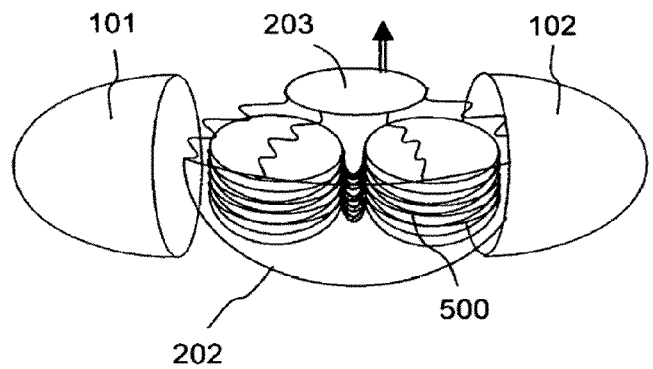
FIGS. 6a-d illustrates another embodiment of the invention.
Figure 6B:
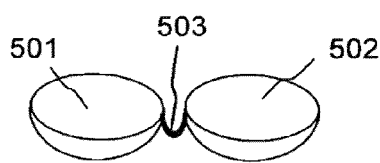
Figure 6C:
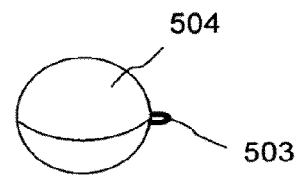
Figure 6D:
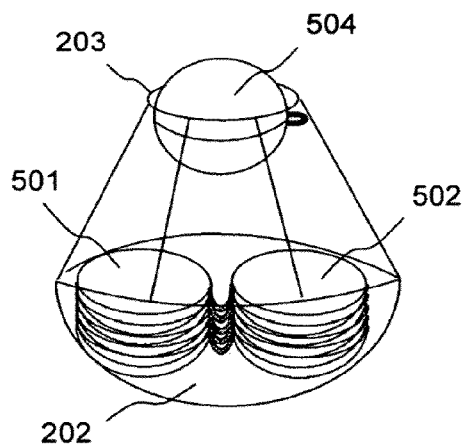

FIG. 2a illustrates the opened external capsule, which opens into two halves 201 and 202 at time t2 (see FIG. 5). It cans also dissolve with control thickness or any other known technique.

FIG. 4a illustrates the assembled capsule being swallowed by the patient at time t1 (see FIG. 5) which is a while after he started his meal at time t0 (see FIG. 5). FIG. 2b is a view of the internal bag 200, FIG. 2c is a view of an expandable bead 301 and FIG. 2d is a view of a coating capsule 400.

FIG. 4b illustrates the dissolution of the external capsule in the stomach 10 at time t2. At this time the super absorbing expandable beads 300 are exposed to the stomach 10 fluids and start absorbing them, as illustrated in FIG. 4c and continue at time period t3 (see FIG. 5).

Figures 4E, 4F:
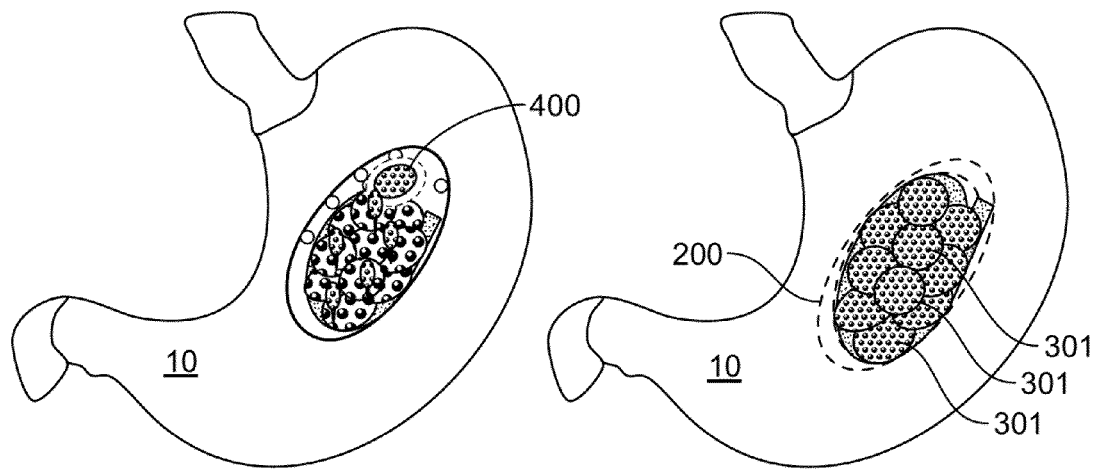
FIG. 4e illustrates the rupture of the coating capsule at t4.
FIG. 4f illustrates the internal capsule dissolving at t5.

Optionally, after the expandable beads 300 fill out the space allowed by the internal bag 200, as illustrated in FIG. 4d, they press against the coating capsule(s) 400. This triggers at time t4 (see FIG. 5) the rupture, as illustrated in FIG. 4e, or dissolution of the coating capsule(s) 400, which contains an agent that coats and seals (see FIG. 4f) all the expandable beads such that they and their content remains untouched throughout their migration down the GI tract.

Figures 4G, 4H:
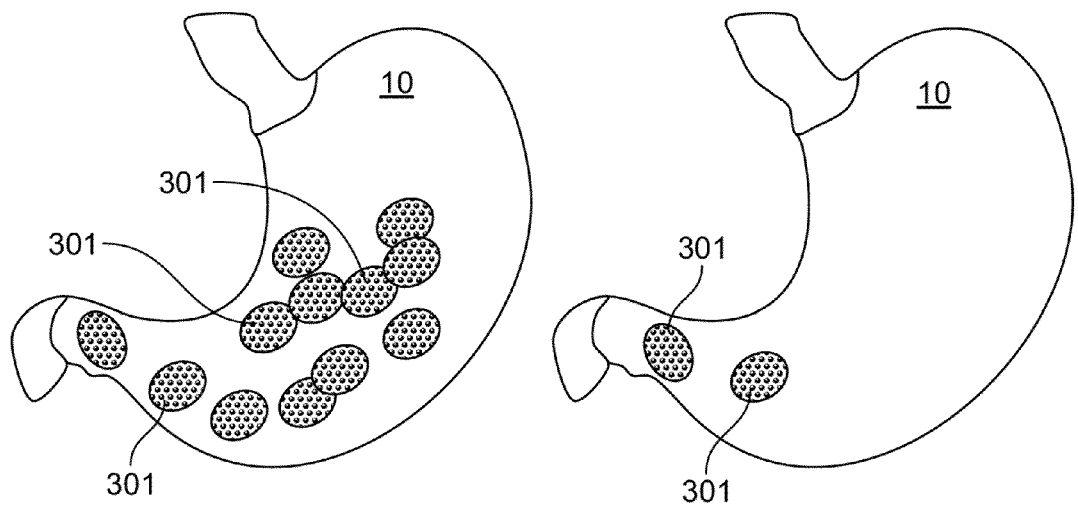
FIG. 4g and FIG. 4h illustrate the draining stage of the coated at t6.

Once all the expandable beads 300 are coated, at time t5 (see FIG. 5), the internal bag dissolves, all the expandable beads are free to move about the GI tract, at time period t6 (see FIG. 5), and they are drained untouched through and out of the GI tract, as illustrated in FIGS. 4g and 4h. The expandable beads 300 dissolve after a preset number of days, in case they were not able to clear out of the GI tract. In another option, the patient drinks a liquid that dissolves expandable beads 300.

Thus the content of the expandable beads 300 which contains ingested food remains untouched, is not digested and absorbed by the body and hence reduces the calorie efficiency of the meal.

In another embodiment of this invention, time t5 (see FIG. 5), when the internal bag 200 dissolves and the expandable beads 300 are free to move about the GI tract, occurs only after the fed mode of the stomach 10 is finished, and the stomach 10 goes into its maintenance mode.

In another embodiment (not shown) the fluids pass on their way to the super absorbable beads through a filter which is wide on the outer side and narrow in the inner side. This makes it easy for the fluids the flow inward the beads and hard to flow back.

In yet another embodiment of this invention, a polymer capable of absorbing lipid having an prolonged equilibrium period in the range of 4-8 hours so as to keep the absorption step active during the relevant period in the digestion tract, is provided. One such polymer for example is Polypore, having high absorption ratio of 13 gr lipid to 1 gr polymer.

Another embodiment of the present invention is to interfere with the micelles which are necessary for the lipid digestion activity. The purpose of the polymer is to disassemble the micelles and extract the lipids. Such a polymer is, for example, isss Gantrez® series, especially Gantrez 225 and Gantrez 425.

So when a mixture of Polypore and Gantrez are introduced to the small intestine, the Gantrez will interfere with the micelle formation equilibrium, and the polypore will absorb the free lipids without the highly competitive back extraction mechanism.

Another embodiment of this invention is illustrated in FIGS. 6a-6d in this embodiment the inner bag is in the form of a folded basket 202 which contains a stack of spheres 500 each of which is split into to halves 501 and 502 which are connected by a spring like connection 503 that the force embedded in it will close up the spheres to the poison 504 in a relaxed mode. When the external capsule 100 dissolves, the force embedded in the stacked up halve spheres 500 will cause the optional basket 202 to open up optionally locked into the position illustrated in FIG. 6d. This allows the half spheres to close up to position 504 which scoops up the food being digested while closing up. The sphere 504 is now small enough to leave the basket 202 through the opening 203, being pushed by the next pair of half spheres. The last pair of half spheres in the stack may remain in the basket 202, which dissolves after a preset time and clears out down the GI tract. The optional basket 202 is designed to avoid the possibility that the closing sphere will harm the stomach 10 inner walls. The spheres 500 are of a size appropriate to be able to travel through the GI tract. The closed spheres are made of a substantially ingestible biocompatible material and remain closed and untouched through the journey down and out of the GI tract. The spheres 500 dissolve after a preset number of days, in case they were not able to clear out of the GI tract. In another option, the patient drinks a liquid that dissolves spheres 500.

Figure 7A:
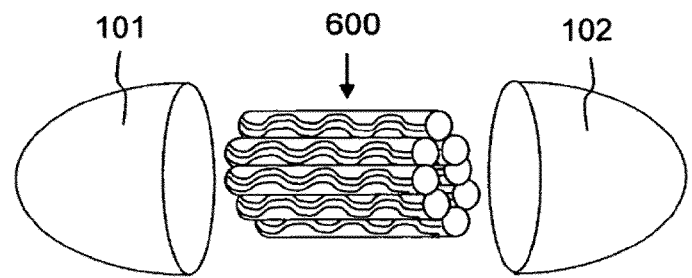
FIGS. 7a-c illustrates another embodiment of the invention.
Figure 7B:
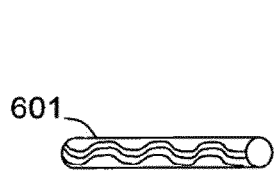
Figure 7C:
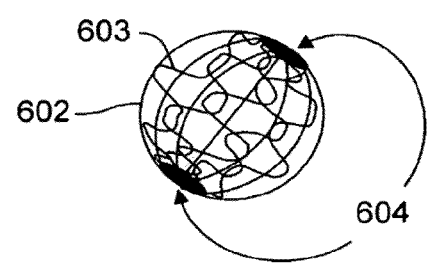

Another embodiment of this invention is illustrated in FIGS. 7a-7c. In this embodiment, the capsule is filled up with number of folded stent like structures 600. When the external capsule 100 dissolves, a force will cause the stents 600 to open up and lock into the position illustrated in FIG. 7c. The force can be embedded in the structures 600, apply via external or internal spring (not shown) or generated internally or externally via chemical reaction with the stomach 10 content. While stents 600 open up inside the stomach 10 they will suck up some of the content into the stents. The stents 600 are built such that they have entry holes 604 through which the content is sucked up. Optionally, entry holes 604 are equipped with a directional valve such that the stomach 10 content can only enter into the stents but can not escape. The size of the opened stents 600 is designed to be able to travel through the GI tract. The stents are made of a substantially ingestible material and remain closed and untouched throughout their journey down and out of the GI tract. The folded structures 601, 602, 603 can also he polymer beads and the force applied to them before delivery to compress the beads substantially so that they open inside the GI tract to capture various liquids. One such polymer, for example, is Polypore, having high absorption ratio of 13 gr lipid to 1 gr polymer and high ratio of its free form volume to its compressed form volume.

Figure 9:
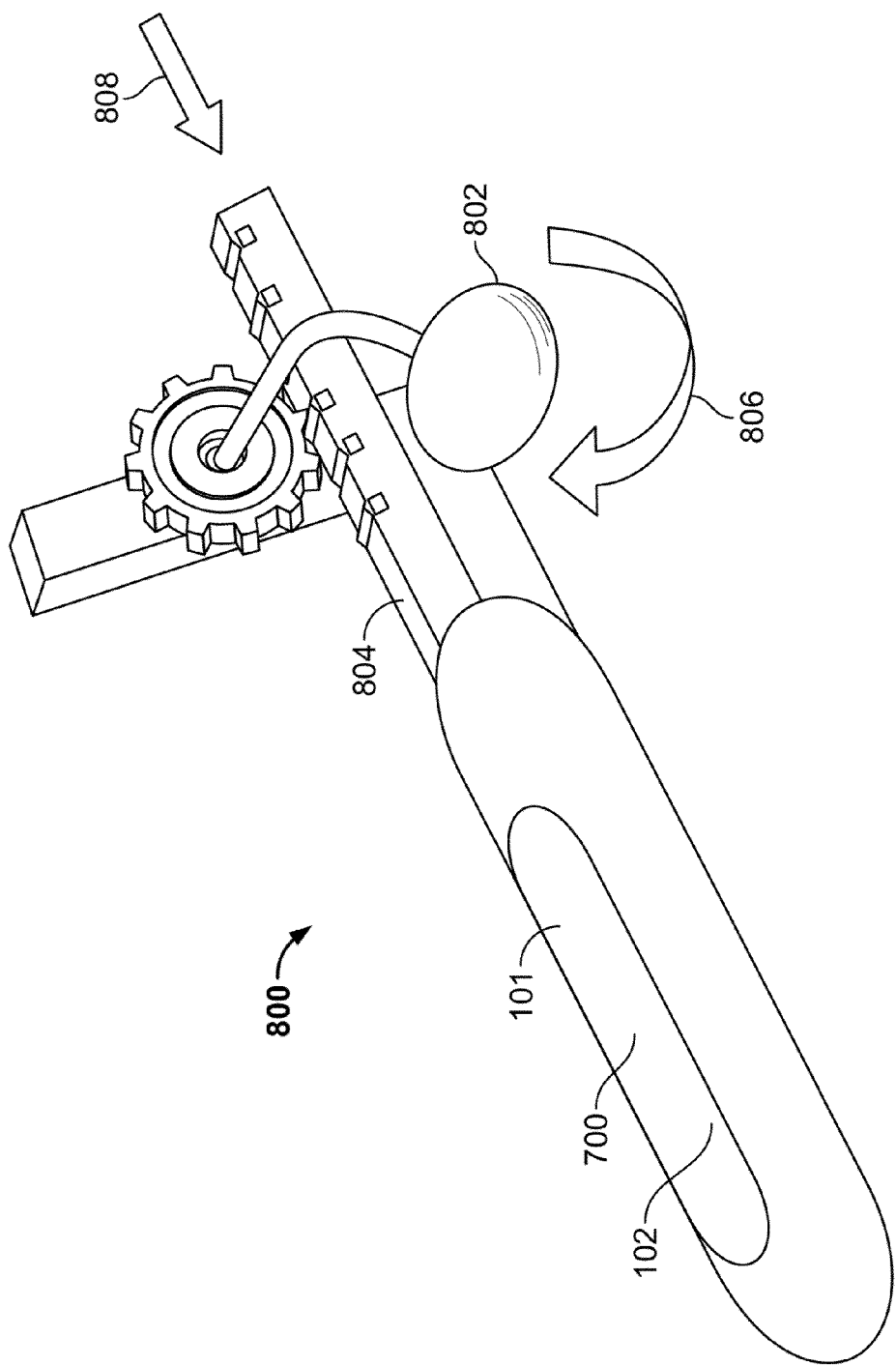
FIG. 9 illustrates an embodiment for loading the force into the small structures.

In another embodiment the force (such as spring force or elastic force) is being loaded into the small structures 700 before using the capsule. FIG. 9 shows a device 800 for compressing the small structures 700 and encapsulating them to form the pill to be swallowed. Turning the handle 802 in direction 806 moves the bar 804 in direction 808. The capsule half 101 is pushed towards the second half 102 and the small structures 700 are compressed. This will overcome the possibility that the force will deteriorate over time.

Another embodiment of this invention is illustrated in FIGS. 8a-8c. In this embodiment, the capsule is filled up with a number of folded structures 700. When the external capsule 100 dissolves, the force embedded within the structures will cause the structures 700 to open up into the position 702 illustrated in FIG. 8c. The force can be embedded in the structures 700, in the manufacturing process by taking a semi rigid structure and forcing it into a collapsed form by applying pressure. The kinetic energy stored in the structures 700 will be used to restore the structures into their natural form once the capsule 100 has opened up. This force is designed so that it can over come the pressure inside the stomach 10. While structures 700 open up inside the stomach 10 they will suck up some of the content into the structures 700. The structures 700 are made up such that they have entry holes 703 through which the content is sucked up. Optionally, entry holes 703 are equipped with a directional valve such that the stomach 10 content can only enter into the structures 700 but cannot escape. The size of the opened stents 700 is designed to be able to travel through the GI tract. The full structures 700 are made of a substantially ingestible material and remain closed and untouched throughout the journey down and out of the GI tract.

In another embodiment the folded structures are polymer beads and the force applied to them before delivery to compress the beads substantially so that they take less space on the intake but open inside the GI tract to capture various liquids. One such polymer, for example, is Polypore, having high absorption ratio of 13 gr lipid to 1 gr polymer and high ratio of its free form volume to its compressed form.

The invention being thus described in terms of several examples and embodiments, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for containing a volume of gastrointestinal (GI) tract content, the method comprising:
   dissolving a capsule in the GI tract, wherein the capsule contains a plurality of expandable structures;
   releasing the plurality of expandable structures into the GI tract, wherein the release is caused by the dissolution of the capsule in the GI tract, and wherein the releasing comprises expanding internal and external volumes of each of the plurality of expandable structures; and
   opening a self-opening barrier of each of the plurality of expandable structures, wherein the opening of each self-opening barrier is caused by the expansion of the respective expandable structure, and wherein opening a self-opening barrier of each of the plurality of expandable structures comprises sucking GI tract content into each of the plurality of expandable structures.

2. The method of claim 1, further comprising closing each of the self-opening barriers, wherein a self-opening barrier is closed when the respective expandable structure is filled with GI tract content.

3. The method of claim 1, wherein the self-opening barriers comprise entry holes, and wherein the GI tract content is sucked in through the entry holes.

4. The method of claim 1, wherein the self-opening barriers comprise directional valves.

5. The method of claim 1, further comprising retaining the GI tract content in the plurality of expandable structures, wherein the GI tract content does not escape the plurality of expandable structures.

6. The method of claim 1, wherein the plurality of expandable structures journey throughout and out of the GI tract.

7. The method of claim 6, wherein the respective self-opening barriers are closed when the plurality of expandable structures journey throughout and out of the GI tract.

8. The method of claim 1, wherein the plurality of expandable structures are polymer structures.

9. A device for containing a volume of gastrointestinal (GI) tract content, the device comprising:
   a capsule, wherein the capsule dissolves in the GI tract;
   a plurality of expandable structures, the plurality of expandable structures packed into the capsule, wherein the plurality of expandable structures are released into the GI tract when the capsule dissolves, and wherein internal and external volumes of each of the plurality of expandable structures expand when the plurality of expandable structures are released; and
   self-opening barriers on each of the plurality of expandable structures, wherein the self-opening barriers open when the respective expandable structures expand, and wherein the self-opening barriers suck GI tract content into the respective expandable structures when opened.

10. The device of claim 9, wherein the plurality of expandable structures are polymer structures.

11. The device of claim 9, wherein the plurality of expandable structures are stents, and wherein the self-opening barriers comprise directional valves.

12. The device of claim 9, wherein the device contains GI tract content that weighs at least 5 times the device weight.

13. A method of containing a solid element within the gastrointestinal (GI) tract comprising:
   delivering a capsule containing a first malabsorption device to the GI tract, wherein the capsule is dissolvable in the GI tract, and wherein the first malabsorption device comprises:
      a first element having a first opening and a first volume, and
      a second element having a second opening and a second volume, the first element flexibly attached to the second element, and wherein
      the capsule maintains the first element and the second element in a first configuration of the first malabsorption device, wherein the first opening is away from the second opening;
   closing the first malabsorption device from the first configuration to a second configuration, the closing caused by the dissolution of the capsule in the GI tract, wherein the first opening is directly adjacent to the second opening such that the first volume and the second volume form a closed aggregate volume when the first malabsorption device is closed in the second configuration.

14. The method of claim 13, wherein the first volume forms a closed volume with the second volume when the first malabsorption device is closed.

15. The method of claim 13, wherein the closing further comprises scooping up GI tract content with the first element.

16. The method of claim 13, wherein delivering comprises stacking the first malabsorption device on a second malabsorption device into a stack, wherein the first malabsorption device and the second malabsorption device are contained in the capsule, and sending the stack to the stomach.

* * * * *